United States Patent [19]

Ryang

[11] Patent Number: 4,595,732

[45] Date of Patent: Jun. 17, 1986

[54] SILOXANE IMIDE DIOLS AND SILOXANE IMIDE ORGANIC BLOCK POLYMERS OBTAINED THEREFROM

[75] Inventor: Hong-Son Ryang, Camarillo, Calif.

[73] Assignee: General Electric Company, Schenectady, N.Y.

[21] Appl. No.: 604,570

[22] Filed: Apr. 27, 1984

[51] Int. Cl.$^4$ .................... C08G 63/18; C08G 63/62; C08G 73/14
[52] U.S. Cl. ................................. 525/417; 525/410; 525/411; 525/418; 525/431; 525/433; 525/436; 528/26; 528/28; 528/29; 528/353; 548/406; 549/214
[58] Field of Search .................... 528/26, 28, 29, 353; 548/406; 549/214; 525/410, 411, 417, 418, 431, 433, 436

[56] References Cited

U.S. PATENT DOCUMENTS 4,381,396  4/1983  Ryang .................... 549/237
4,404,350  9/1983  Ryang .................... 528/26

*Primary Examiner*—Lester L. Lee
*Attorney, Agent, or Firm*—William A. Teoli; James C. Davis, Jr.; James Magee, Jr.

[57] ABSTRACT

Siloxane norbornane imide bisphenols are provided and method for making such materials. The siloxane-imide norbornane bisphenols can be used to make a variety of siloxane-imide organic block polymers useful as high performance thermoplastics.

10 Claims, No Drawings

SILOXANE IMIDE DIOLS AND SILOXANE IMIDE ORGANIC BLOCK POLYMERS OBTAINED THEREFROM

CROSS REFERENCE TO RELATED APPLICATIONS

Reference is made to my copending application Ser. No. 596,187, for Silicon Functionalized Norbornene Carboxy Imides and Methods for Making, filed Apr. 2, 1984 and application Ser. No. 604,569, for Heat Curable Silicon Polyimide Block Copolymers, filed concurrently herewith, where both applications are assigned to the same assignee as the present invention and incorporated herein by reference.

BACKGROUND OF THE INVENTION

Prior to the present invention, one method for making siloxane diols, for example, siloxane bisphenols, were made by effecting reaction between polydiorganosiloxane having terminal silicon hydride siloxy units and a phenol having a nuclear bound aliphatically unsaturated group, such as allylphenol, in the presence of a platinum catalyst. Accordingly, Vaughn, U.S. Pat. No. 3,419,635, assigned to the same assignee as the present invention shows the addition of allylphenol to a polydimethylsiloxane having terminal silicon hydride dimethylsiloxy units. The resulting polydiorganosiloxane having terminal siloxy units with phenol groups attached to silicon by silicon-carbon linkages can thereafter be reacted with phosgene to produce a silicon-polycarbonate block copolymer. if desired, some of these silicone-polycarbonate block copolymers can be used in the preparation of room temperature vulcanizable organopolysiloxane-polycarbonate compositions.

The present invention is based on the discovery that siloxane imide diols having the formula

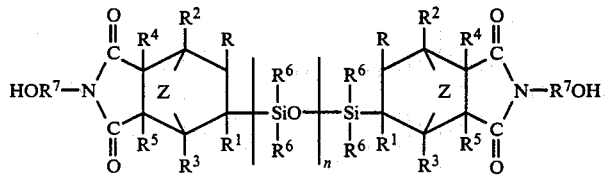

(1)

can be used to make siloxane-imide-organic block copolymers having chemically combined polyester or polycarbonate blocks, where R–R$^5$ are members selected from hydrogen, halogen, C$_{(1-13)}$ monovalent hydrocarbon radicals and substituted C$_{(1-13)}$ monovalent hydrocarbon radicals, Z is selected from —O— and C—(R)$_2$—, R$^6$ is selected from C$_{(1-13)}$ monovalent hydrocarbon radicals and substituted C$_{(1-13)}$ monovalent hydrocarbon radicals, R$^7$ is selected from divalent C$_{(2-13)}$ hydrocarbon radicals and substituted C$_{(2-13)}$ divalent hydrocarbon radicals, and n is a whole number equal to 1–200 inclusive.

STATEMENT OF THE INVENTION

The siloxane imide diols of formula (I) can be made by effecting reaction between a silylnorbornane anhydride of the formula

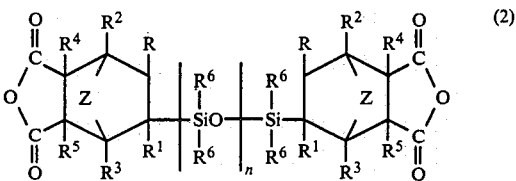

(2)

and an amino organo compound of the formula $$NH_2R^7OH \qquad (3)$$

where R–R$^7$, Z and n are as previously defined.

In addition to the siloxane imide diols of formula (1), there is also included by the present invention, siloxane imide organic block polymers comprising by weight (A) 1 to 99% of siloxane imide organooxy units of the formula,

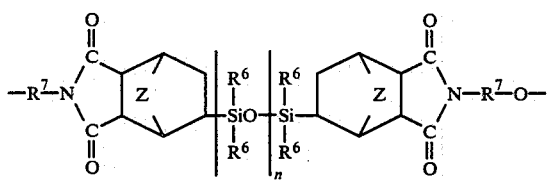

chemically combined with (B) 0 to 99% of organooxy units of the formula $$-R^8O- \qquad (4)$$

where (A), or (A) and (B) are joined through a carbonyl unit selected from (5)

$$-\underset{\underset{O}{\|}}{C}-,$$

$$-\underset{\underset{O}{\|}}{C}-R^9-\underset{\underset{O}{\|}}{C}-,$$

$$-\underset{\underset{O}{\|}}{C}-NH-R^{10}-NH\underset{\underset{O}{\|}}{C}-,$$

and mixtures thereof, where R–R$^7$ are as previously defined, R$^8$ is a C$_{(2-30)}$ divalent organo radical, R$^9$ is a divalent C$_{(6-13)}$ aromatic organic radical and R$^{10}$ is a divalent C$_{(2-13)}$ organo radical.

Radicals included within R–R$^5$ are, for example, hydrogen and halogen such as chloro, bromo, etc.; aryl radicals and halogenated aryl radicals, for example, phenyl, chlorophenyl, tolyl, xylyl, biphenyl, naphthyl, etc.; C$_{(1-8)}$ alkyl radicals, for example, methyl, ethyl, propyl, butyl, octyl, etc. R$^6$ radicals include all of the aforementioned R–R$^5$ except hydrogen and halogen. In addition, R$^6$ radicals also can be alkenyl radicals, for example, vinyl, allyl, cyclohexenyl; haloalkyl such as trifluoropropyl and cyanoalkyl such as cyanoethyl, cyanopropyl, etc.

Radicals included within $R^7$ are, for example, arylene radicals such as phenylene, tolylene, xylylene, naphthalene, alkylene such as dimethylene, trimethylene, tetramethylene, etc. Radicals included within $R^8$ are, for example, alkylene radicals and arylene radicals included by $R^7$. In addition $R^8$ also can be

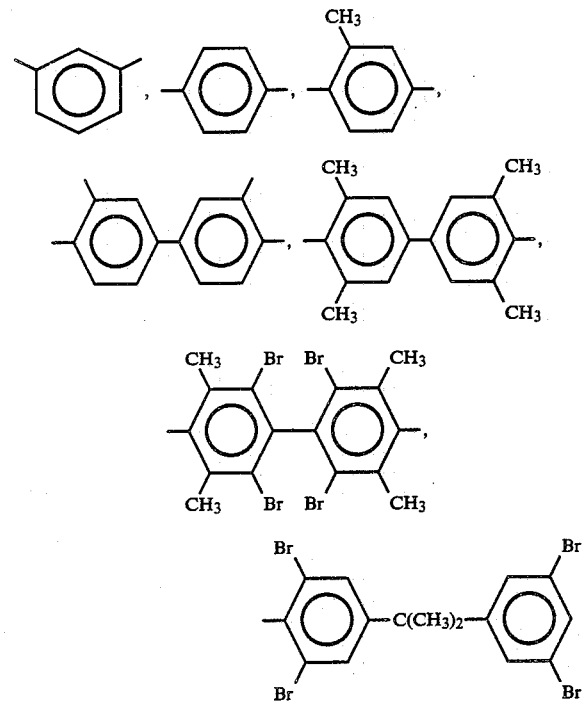

and divalent organic radicals of the general formula,

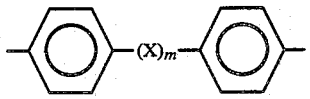

where X is a member selected from the class consisting of divalent radicals of the formulas,

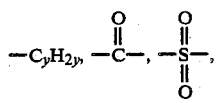

—O—, and —S—, where m is 0 or 1, and y is a whole number from 1 to 5.

Radicals included within $R^9$ are, for example, arylene radicals included within $R^7$. Radicals included within $R^{10}$ are, for example, alkylene and arylene radicals included within $R^7$.

The siloxane imide organic block copolymers of the present invention have been found to be injection moldable thermoplastic materials and useful in a variety of applications where high performance thermoplastic polymers are required. A wide variety of the siloxane organic block copolymers can be prepared utilizing the siloxane imide diols of the present invention by coreacting the siloxane imide diols of formula (1) with diols such as ethylene glycol, 1,4-butanediol, hydroquinone, phenol terminated polyester, polycarbonate, or polysulfone; bisphenols such as bisphenol-A, novolak resins, etc., by use of coreactants such as dichlorides, for example, isophthalic acid chloride, phosgene, and reactants such as toluene diisocyanate, etc.

Those skilled in the art would know that the characteristics of the siloxane imide organic block polymers of the present invention can vary widely depending upon the weight percent of silicon and/or the block size of the polydiorganosiloxane utilized in making the siloxane imide diol. For example, if a siloxane imide diol of formula (1) is employed, where n is 1, it can be equilibrated with a cyclic polysiloxane such as octamethylcyclotetrasiloxane to produce a siloxane imide diol having a polydiorganosiloxane block size of up to 200 units or greater if desired. The siloxane imide organic block polymers of the present invention also can be blended with reinforcing filler, for example, fumed silica, precipitated silica, glass fiber, carbon fiber, etc., where there can be utilized from 1 to 80 parts of filler per 100 parts of the siloxane-organic block copolymer.

In preparing the siloxane imide diols of formula (1), reaction can be effected at temperatures between 45° C.–250° C. and amino organo compound of formula (3), for example o, m, p aminophenol, the corresponding aminocresol, ethanol amine, propanolamine, butanol amine and the silylnorbornane anhydride of formula (2) in the presence of a suitable organic solvent, for example, benzene, o-dichlorobenzene-chlorobenzene mixture, etc. During the reaction, water can be removed azeotropically. The siloxane imide diols can thereafter be purified with silicon gel, column chromatography.

In preparing the siloxane imide organic block polymers, conditions will vary widely depending upon whether phosgenation is used, or terephthaloylchloride, an organic diisocyanate, etc. For example, esterification can be achieved in a mixture of a suitable base such as triethylamine and an inert organic solvent such as chloroform, methylene chloride, chloro-benzene, etc.

In order that those skilled in the art will be better able to practice the present invention, the following examples are given by way of illustration and not by way of limitation. All parts are by weight.

EXAMPLE 1

There was added 10 drops of a 5% platinum catalyst prepared in accordance with Karstedt, U.S. Pat. No. 3,775,442, assigned to the same assignee as the present invention, to a mixture while it was being stirred of 69.4 g (0.42 mole) of 5-norbornene-2,3-dicarboxylic acid anhydride, 26.8 g (0.2 mole) 1,1,3,3-tetramethyldisiloxane and 100 ml of dry chlorobenzene. The resulting mixture was heated with stirring to 70°–80° C. for 4 hours and then 100°–110° C. overnight. After cooling carbon black was added and the solution was stirred for 30 minutes at room temperature. Filtration, removal of the solvent at 100° C. with a vacuum pump and addition of dry diethylether resulted in the precipitation of a white crystalline solid. Based on method of preparation, the product was 5,5'-(1,1,3,3-tetramethyl-1,1,3-disiloxanediyl)-bis-norbornane-2,3-dicarboxylic anhydride having the formula,

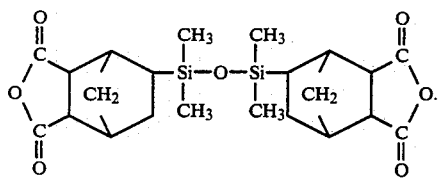

A mixture of 13.65 grams of the above norbornane siloxane dianhydride, 6.7 grams of para-aminophenol, in 150 ml of a mixture of 4 parts of o-dichlorobenzene-chlorobenzene was refluxed for 3 hours under nitrogen during which time water was removed azeotropically. After removal of the solvent, the residue was further heated to 160° C. for 2 hours under vacuum. Crude product was passed through a silica gel column with chloroform as an eluent and recrystallized from a mixture of chloroform and diethylether. There was obtained 16.3 grams or an 84.5% yield of a colorless solvent having a melting point of 240° C. (dec). Based on method of preparation and $^1$H.NMR, the product was a siloxane imide bisphenol having the formula,

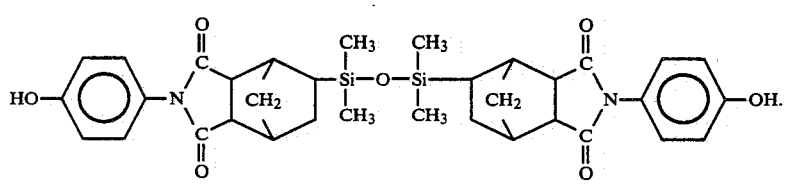

The identity of the above compound was further confirmed by elemental analysis, calculated for $C_{34}H_{40}N_2O_5Si_2$: C, 63.31; H, 6.26; N, 4.34. Found: C, 63.1; H, 6.3; N, 4.2.

EXAMPLE 2

The same procedure was repeated, except that there was utilized 11.41 grams of the siloxane imide dianhydride of Example 1 and 5.5 grams of meta-aminophenol. Purification of the crude product by silica gel column chromatography with chloroform as an eluent, followed by recrystallization from a chloroform diethylether mixture provided 15.1 grams of a 94.4% yield of a colorless solid having a melting point of 220° C. (dec). Based on method of preparation and $^1$H NMR, the product was a bisphenol imide disiloxane of the formula

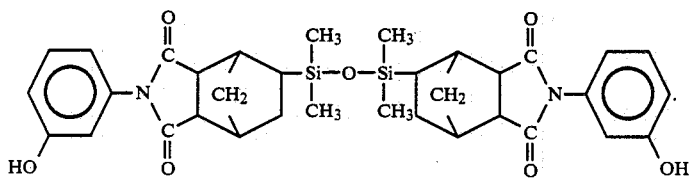

The identity of the above compound was further confirmed by elemental analysis, calculated for a $C_{34}H_{40}N_2O_5Si_2$: C, 63.31; H, 6.26; N, 4.34. Found: C, 63.1; H, 6.4; N, 4.3.

The bisphenol imide disiloxane is incorporated into a CY179 epoxy resin to produce a mixture containing 2% of the bisphenol siloxane imide. The epoxy resin is then blended with 2 parts of benzyl amine per 100 parts of epoxy resin. There is obtained a mixture curable at room temperature and useful for encapsulating electronic components.

EXAMPLE 3

A mixture of 1.28 grams of the siloxane imide bisphenol for Example 1, and 7.1 grams of octamethylcyclotetrasiloxane in 40 ml of dry chlorobenzene containing 5 drops of 98% sulfuric acid was heated to 120° C. over a period of 48 hours while the mixture was vigorously stirred. Carbon black was then added to the mixture and was further heated to 100° C. for 1 hour. The mixture was then filtered and the filtrate was evaporated to dryness in vacuo. The residue was treated with diethylether and the insoluble materials were filtered off. After the solvent was removed, the residue was heated to 150° C. for 2 hours in vacuo which provided 6.5 grams or a 78% yield of a bisphenol terminated polydimethylsiloxane having the average formula

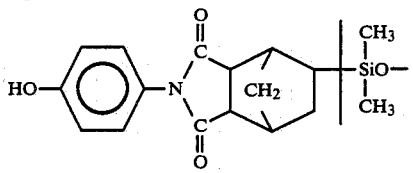

where n is 18.

The identity of the product was confirmed by $^1$H NMR and $^{29}$SiNMR showed that the number average molecular weight of the product was 5,080.

The same procedure was repeated, except that there was utilized 1.28 grams of the bisphenol siloxane imide of Example 2 and 7.1 grams of the octamethylcyclotetrasiloxane. There was obtained 6.8 grams of product or a yield of 82% of a colorless, viscous oil. The product has the following average formula

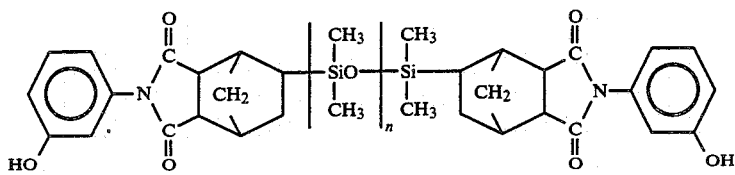

where n is 16.

The identity of the above product was confirmed by $^1$H NMR and IR. Its number average molecular weight was 4,800, which was determined by $^{29}$SiNMR.

EXAMPLE 4

There was slowly added 1 mmole of terephthaloyl chloride in methylene chloride to a mixture of 1 mmol of the bisphenol siloxane imide of Example 1, and 2 mmols of triethylamine in 100 ml of dry chloroform. The addition of the terephthaloyl chloride was conducted over a 10 minute period at room temperature. The resulting solution was stirred at room temperature for 24 hours. After evaporation of the solvents, the residue was heated to 150° C. for 30 minutes in vacuo. The crude product was dissolved in chloroform and poured into 150 ml of methanol under vigorous stirring. A product precipitated and it was collected on a filter, washed repeatedly with methanol and distilled water. The product was then dried in a vacuum at 60° C. There was obtained a 94% yield of a material having an intrinsic viscosity of 0.55 in chloroform. Based on method of preparation, the product was a siloxane imide ester block copolymer consisting essentially of chemically combined units of the formula,

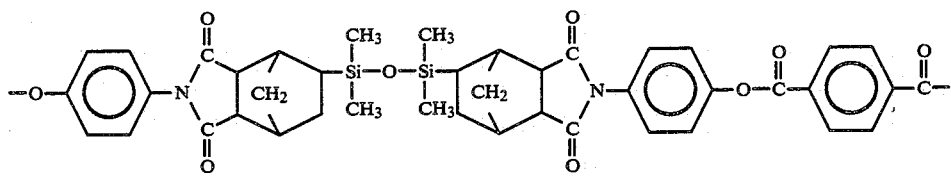

The same procedure was repeated, except the bisphenol siloxane imide of Example 2 was used to make the corresponding siloxane imide ester block copolymer. There was obtained a yield of 93% and the block copolymer had an intrinsic viscosity of 0.22 in chloroform.

The above block copolymers made from the bisphenol siloxane imides of "Example 1" and "Example 2" had the following properties:

| Block Copolymer | Tg (°C.) | TGA (°C.) 10% Wt Loss | |
|---|---|---|---|
| | | N$_2$ | Air |
| Example 1 Bisphenol | 205 | 455 | 450 |
| Example 2 Bisphenol | 166 | 450 | 450 |

EXAMPLE 5

There was slowly added 1 mmol of terephthaloyl chloride to a mixture of 0.1 mmol of the phenol terminated polydimethylsiloxane of Example 3, and 0.9 mmol of bisphenol-A suspended in dry methylene chloride along with 2 mmols of triethylamine. The resulting solution was stirred at room temperature for 24 hours. The solvent was then evaporated from the mixture and the residue was heated to 150° C. for 30 minutes in vacuo. The product was obtained in a 93.4% yield and it had an intrinsic viscosity in chloroform of 0.68 and a TG of 1.78. Based on method of preparation, the product was a siloxane imide ester block copolymer consisting essentially of units of the formula,

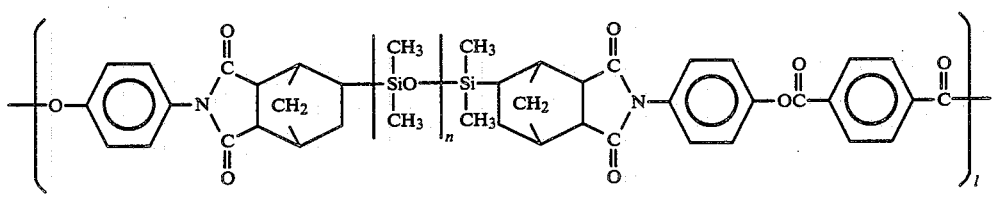

chemically combined with

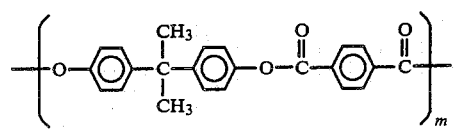

where l=1, m=9 and n=61.

The above procedure was repeated, except that a meta-substituted bisphenol imide polydimethylsiloxane was utilized in making the siloxane imide ester block copolymer. There was obtained a siloxane imide ester block copolymer similar to the above formula, except it had meta-bisphenol units and l=2, m=8 and n=57.

The following table shows additional properties of the siloxane imide ester block copolymers of Example 5, where IV is intrinsic viscosity, Tg and Tm are glass transition and melting temperatures and TGA is thermogravimetric analysis:

TABLE

| Bisphenol | IV | °C. | | TGA (°C.) 10% WT Loss | |
|---|---|---|---|---|---|
| | | Tg | Tm | $N_2$ | Air |
| para | 0.68 | 178 | | 450 | 425 |
| meta | 0.55 | 156 | 272 | 410 | 420 |

The above results show that the silicone organic block polymers of the present invention are valuable injection moldable thermoplastics which can be employed in a variety of applications.

Although the above examples are directed to only a few of the very many variables within the scope of the present invention, it should be understood that the present invention is directed to a much broader variety of bisphenol siloxane imides and silicone organic block polymers which can be made by effecting reaction between the siloxane silicon imide diols of formula (1) with various coreactants such as dihydric phenols or glycols or mixtures thereof in combination with coreactants such as phosgene, terephthaloyl chloride, toluene diisocyanate, etc.

What I claim as new and desire to secure by Letters Patent of the United States is:

1. Siloxane imide diols having the formula,

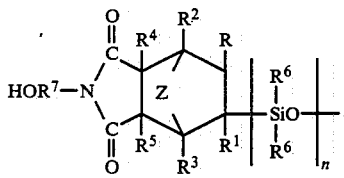

-continued

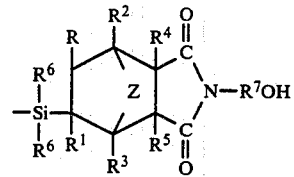

where $R-R^5$ are members selected from hydrogen, halogen, $C_{(1-13)}$ monovalent hydrocarbon radicals and halogenated $C_{(1-13)}$ monovalent hydrocarbon radicals, Z is selected from —O— and $C-(R)_2$—, $R^6$ is selected from $C_{(1-13)}$ monovalent hydrocarbon radicals, halogenated $C_{(1-13)}$ monovalent hydrocarbon radicals and cyanoalkyl radicals, $R^7$ is selected from divalent $C_{(2-13)}$ hydrocarbon radicals and n is an integer equal to 1–200 inclusive.

2. A siloxane imide bisphenol having the formula,

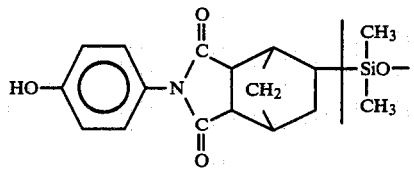

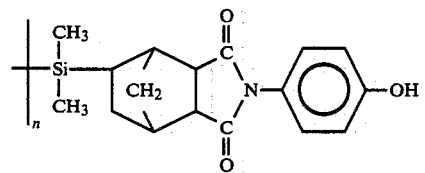

where n is 1 to 200 inclusive.

3. A siloxane imide-bisphenol having the formula,

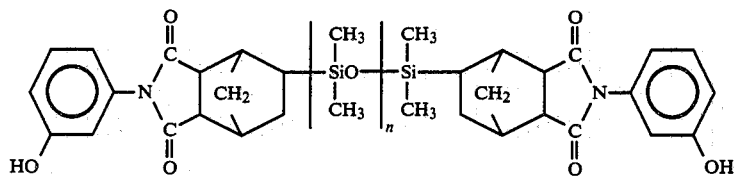

where n is 1 to 200 inclusive.

4. A siloxane imide bisphenol having the formula,

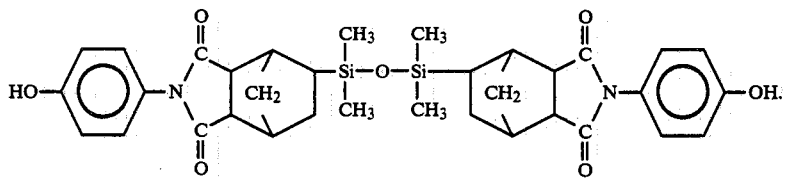

5. A siloxane imide bisphenol having the formula,

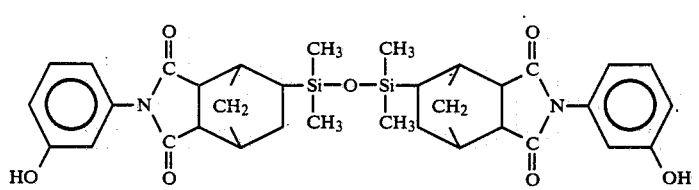

6. A method for making a siloxane imide bisphenol which comprises effecting reaction between a silylnorbornane anhydride having the formula,

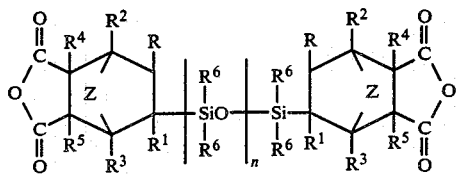

and an aminoorgano compound having the formula,

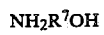

where $R-R^5$ are members selected from hydrogen, halogen, $C_{(1-13)}$ monovalent hydrocarbon radicals and halogenated $C_{(1-13)}$ monovalent hydrocarbon radicals, Z is selected from —O— and C—$(R)_2$—, $R^6$ is selected from $C_{(1-13)}$ monovalent hydrocarbon radicals, halogenated $C_{(1-13)}$ monovalent hydrocarbon radicals and cyanoalkyl radicals, R is selected from divalent $C_{(2-13)}$ hydrocarbon radicals and n is a whole number equal to 0-200 inclusive.

7. A method in accordance with claim 5, where the silyl norbornane anhydride has the formula,

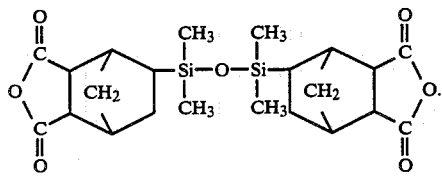

8. Siloxane imide organic block polymers comprising by weight
(A) 1 to 99% of siloxane imide organo-oxy units of the formula,

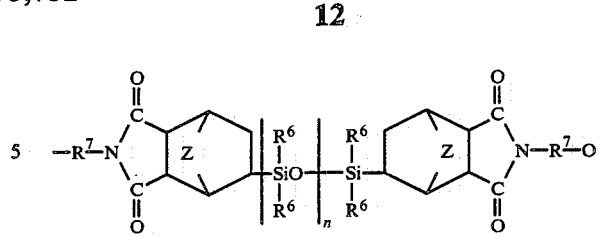

chemically combined with
(B) 0 to 99% of organo-oxy units of the formula $$-R^8O- \quad (4)$$

where (A) and (B) are joined through a carbonyl units selected from

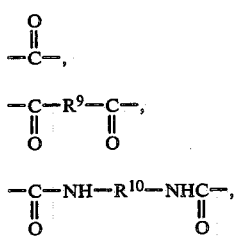

where $R-R^5$ are members selected from hydrogen, halogen, $C_{(1-13)}$ monovalent hydrocarbon radicals and halogenated $C_{(1-13)}$ monovalent hydrocarbon radicals, Z is selected from —O— and C—$(R)_2$—, $R^6$ is selected from $C_{(1-13)}$ monovalent hydrocarbon radicals, halogenated $C_{(1-13)}$ monovalent hydrocarbon radicals and cyanoalkyl radicals, $R^7$ is selected from divalent $C_{(2-13)}$ hydrocarbon radicals $R^8$ is a $C_{(2-30)}$ divalent organo radical, $R^9$ is a divalent $C_{(6-13)}$ aromatic organic radicals and $R^{10}$ is a divalent $C_{(2-13)}$ organo radical, and n is equal to 1-200 inclusive.

9. A siloxane-imide-organic block polymer in accordance with claim 8 consisting essentially of chemically combined units of the formula

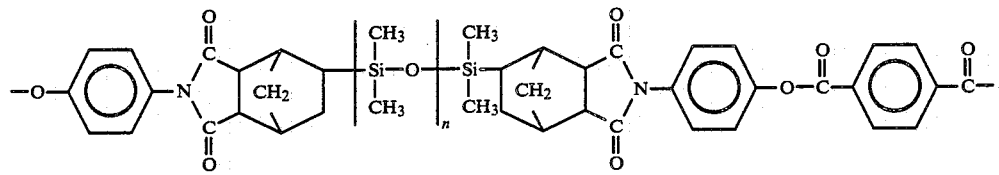

where n is equal to 1 to 200 inclusive.

10. A siloxane-imide-organic block polymer in accordance with claim 8 consisting essentially of chemically combined units of the formula,

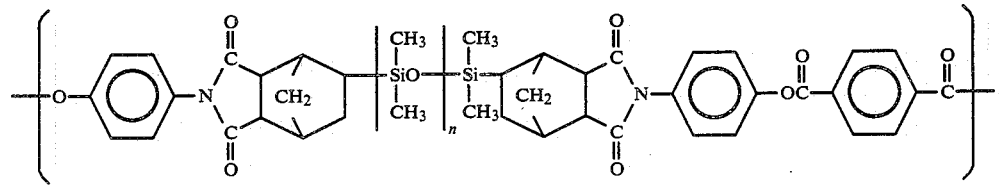

where n is equal to 1 to 200 inclusive.

* * * * *